US008593251B2

(12) United States Patent
Heller

(10) Patent No.: US 8,593,251 B2
(45) Date of Patent: Nov. 26, 2013

(54) SYSTEMS FOR DETECTING A FEBRILE CONDITION AND REDUCING RISKS OF SPREADING INFECTION

(76) Inventor: Alan Camerik Heller, Dallas, TX (US)

(*) Notice: Subject to any disclaimer, the term of this patent is extended or adjusted under 35 U.S.C. 154(b) by 413 days.

(21) Appl. No.: 13/161,771

(22) Filed: Jun. 16, 2011

(65) Prior Publication Data

US 2012/0319847 A1 Dec. 20, 2012

(51) Int. Cl.
*G05B 19/00* (2006.01)

(52) U.S. Cl.
USPC .................. 340/5.2; 340/539.12; 340/603

(58) Field of Classification Search
USPC ........ 340/573.1, 5.2, 584, 603, 539.12, 573.5
See application file for complete search history.

(56) References Cited

U.S. PATENT DOCUMENTS

| | | | | |
|---|---|---|---|---|
| 5,299,594 | A * | 4/1994 | Lord et al. | 137/101.19 |
| 5,339,687 | A * | 8/1994 | Gimson et al. | 73/204.19 |
| 5,499,631 | A * | 3/1996 | Weiland | 600/547 |
| 6,677,859 | B1 * | 1/2004 | Bensen | 340/604 |
| 8,073,535 | B2 * | 12/2011 | Jung et al. | 600/547 |
| 2004/0220538 | A1 * | 11/2004 | Panopoulos | 604/361 |
| 2007/0222554 | A1 * | 9/2007 | Hart | 340/5.6 |
| 2009/0284380 | A1 * | 11/2009 | Chen et al. | 340/584 |
| 2011/0050432 | A1 * | 3/2011 | Macsween et al. | 340/603 |

* cited by examiner

*Primary Examiner* — Travis Hunnings
(74) *Attorney, Agent, or Firm* — John Lindsay

(57) ABSTRACT

The technology provides an external device for estimating a core body temperature of a human subject, and a system for use in a local area, such as a school, hospital, workplace, and the like. The wrist monitor device includes a casing sized and shaped to fit onto a wrist of a human subject. The casing has a first face and a second face. In addition there is a cavity in the casing that houses a heat trap. The heat trap has an opening oriented to receive incoming thermal energy and a shell of a thermal-insulation material that has an inner thermal energy-reflective surface. Detected temperature data is compiled in a database and used to estimate whether an identified individual has a core body temperature indicative of a fever. There is also provided a system for identifying persons and screening the persons for a febrile condition. The system may include the steps of: identifying a person using data input by the individual or detected from indicia of the person and previously stored data about the person; detecting a temperature condition of the person; determining whether the person has a febrile condition using the detected temperature condition and previously stored temperature data of the person; and taking action to restrict ingress, deny ingress or allow ingress, based on the determined febrile condition of the person requiring ingress.

6 Claims, 7 Drawing Sheets

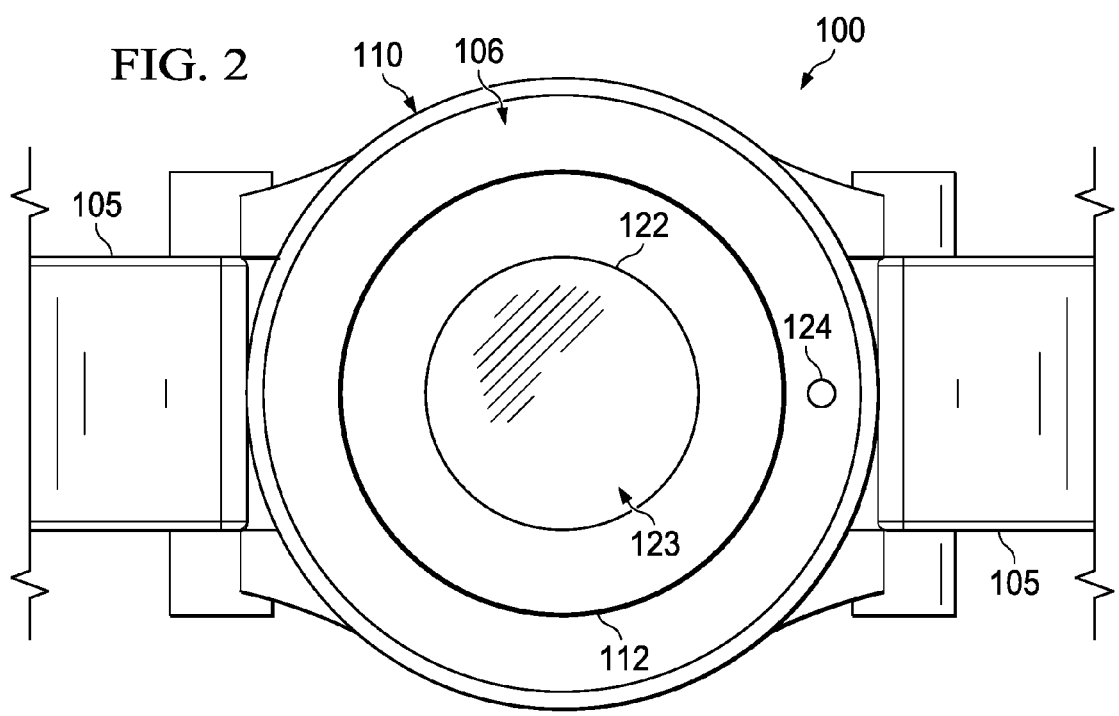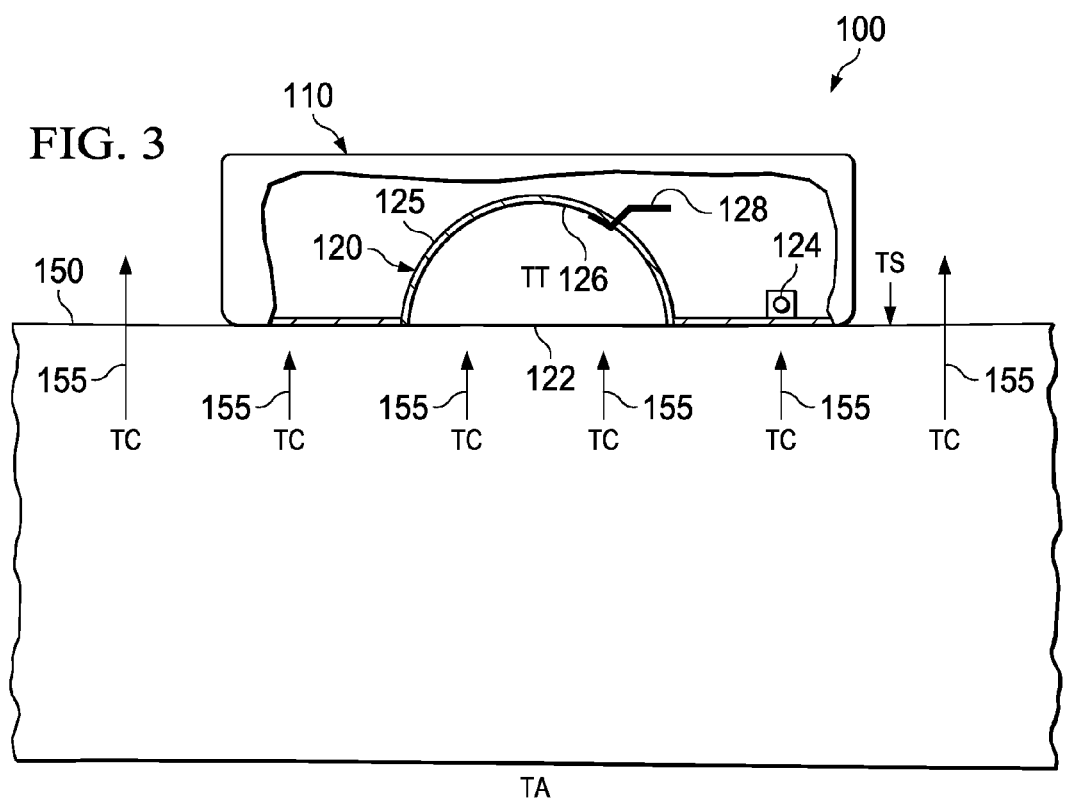

SYSTEMS FOR DETECTING A FEBRILE CONDITION AND REDUCING RISKS OF SPREADING INFECTION

BACKGROUND

1. Field of the Invention

The technology relates to systems for scanning to determine a febrile condition in a human subject as a preliminary parameter to allow or deny ingress to a protected facility, and more particularly, it relates to a system for accumulating and processing temperature data to identify individuals exhibiting a temperature condition indicating an actual or potential health condition.

2. Description of the Related Art

It has been become increasingly necessary to detect and identify people that may be infected with a contagious illness, whether bacterial or viral. People are very mobile, traveling from city to city and country to country, and that factor makes it even more important to identify infected persons, to prevent or at least minimize the potential for the spread of disease. In recent years there has been mounting concern about such international infectious diseases as SARS in recent years, and concerns about infections transmitted in hospitals, among others. There is a consensus that elimination of transmission of a contagion through detection and isolation of infected individuals may be an effective tool in avoiding the spread of the contagion. However, there does not appear to be a ready solution to the issue of identification of the infected individual.

It is well known that most infectious diseases produce an increase in core body temperature in the host. This is often also the earliest sign of the infection. Accordingly, measuring core body temperature and monitoring it in facilities such as work places, hospitals, school, and other places where large numbers of people congregate or interact may pose a potential for identifying and isolating potentially infected persons and preventing or reducing the risk of transmission of the infection. Measuring core body temperature, unlike measurement of body surface temperature, poses several challenges, however. Core body temperature measurements are typically taken in an invasive procedure, for example, use of an oral thermometer, or infra-red device inserted into an ear cavity. Accordingly, it is challenging to carry out such monitoring on a periodic basis for large groups of people. Indeed, it is quite likely that individuals may resist such procedures. Measuring surface temperature is much easier and can be done via an infra-red scanner. But, merely measuring a surface body temperature is not generally as reliable an indicator of infection because it is influenced by external conditions, such as ambient temperature, clothing, etc. The core body temperature, poses challenges as well because core body temperature varies from one individual to another as an inherent condition of the individual. But, for each individual, core body temperature will increase when an infectious agent is present and the body's defenses are activated in response. Thus, core body temperature is a much better indicator of infection for an individual and may be used with a high degree of confidence for that individual when there is a reliable "base line" of temperature data for that individual.

SUMMARY

An exemplary embodiment provides a system for identifying individuals and screening the individuals for a febrile condition. The system includes the steps of identifying a person using data input by the individual or detected from indicia of the person and previously stored data about the person. Further it includes detecting a temperature condition of the person. Using the temperature condition and previously stored temperature data about the person, the system determines whether the person has a febrile condition. Based on the result, the system allows taking action to restrict ingress, deny ingress or allow ingress based on the determined condition of the person requiring ingress. Optionally, the system includes providing an alarm when a person requiring ingress has a febrile condition. Also optionally, the step of transmitting read temperature data may include transmitting the read temperature data to a first transmitter so that the first transmitter then transmits the read data to a server.

An exemplary embodiment of the technology also provides an external device for estimating a core body temperature of a human subject. The device includes a casing sized and shaped to fit onto a wrist of a human subject. The casing has a first face and a second face. In addition there is a cavity in the casing that houses a heat trap. The heat trap is located adjacent to the first face of the casing and has an opening oriented to receive incoming thermal energy. The heat trap has a shell of a thermal-insulation material that has an inner thermal energy-reflective surface. There is a first temperature sensor extending into or along the shell to measure a temperature within the heat trap, and a second temperature sensor at a peripheral region of the casing. A transmitter is in communication with the first and second temperature sensors to transmit temperature data. A power source is located in the cavity within the casing to power the transmitter.

Optionally, the device may include a graphic user interface in the second face of the casing interface displaying information, such as sensor-detected temperature information. Further optionally, the shell may be dome-shaped. And, the inner thermal energy-reflective surface of the shell may be of metallic foil. Optionally, the first temperature sensor may be a thermistor. And, optionally, a wrist band may extend from the casing to secure the casing to a human wrist such that the first face interfaces with an inner side of the wrist. Optionally, the transmitter may be selected from a radio-frequency transmitter, a WiMax transmitter and a Bluetooth transmitter. Further, the device may include a microprocessor receiving input from the first and second temperature sensors, converting the input to a form of digital information, and relaying the digital information to the transmitter. In addition, a shield of a thermal energy transmissive material may cover the opening of the heat trap.

Another exemplary embodiment of the technology provides a system for the detection of a fever in a human subject. The system has a number of features, and includes a wrist monitor with a transmitter, a receiver, a digital database, a processor, and an interface. The wrist monitor is sized and shaped to fit onto a wrist of a human subject. In addition, the wrist monitor includes a casing having a first face and a second face, and a cavity in the casing that houses a heat trap. The heat trap includes a shell of a thermal-insulation material with an inner thermal energy-reflective surface. The heat trap has an opening oriented to receive incoming thermal energy. The wrist monitor also has a first temperature sensor extending into or along the heat trap to measure a temperature within the shell, and a second temperature sensor at a peripheral region of the casing. The monitor includes a first transmitter in communication with the first and second temperature sensors to transmit data comprising temperature data and human subject identifying data, and a power source within the casing to power the first transmitter. The system has a receiver communicating with the first transmitter and receiving the temperature data and the human subject identifying data. The system further has a database configured to store temperature data for a plurality of human subjects and a processor determining whether a human subject has a fever, based on the received data. There is also an interface in communication with the processor that is configured to communicate whether a human subject has a fever.

Optionally, the receiver may be part of a hand-held device that includes a second transmitter. The second transmitter transmits received temperature and identifying data by WiFi, WiMax or digital telephony to a server comprising the digital database. Optionally, the first transmitter is selected from a radio-frequency transmitter, a WiMax transmitter and a Bluetooth transmitter.

BRIEF DESCRIPTION OF THE DRAWINGS

The following drawings are not to scale and are provided for ease of explanation. The Figures depict exemplary embodiments, and do not limit the scope of the invention, as defined in the Claims, here below:

FIG. 2 is a schematic view of the underside of an exemplary embodiment of a core body temperature wrist monitor;

FIG. 3 is a schematic partial cross sectional view of an exemplary embodiment of a core body temperature wrist monitor as worn on a user's wrist, showing an exemplary heat trap with arrows depicting thermal energy flow;

DETAILED DESCRIPTION

Figure 1:
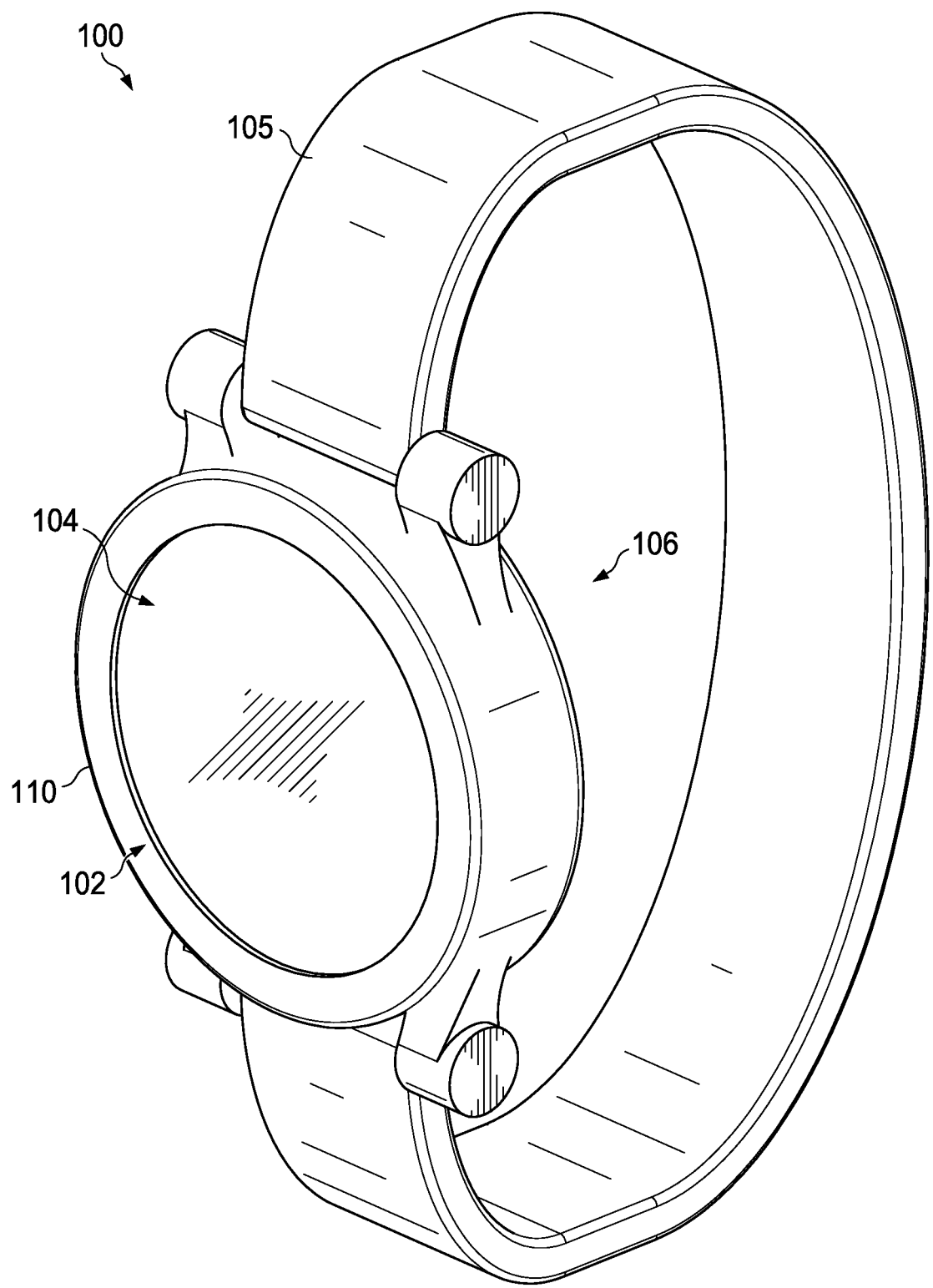
FIG. 1 is a schematic view of the exterior of an exemplary embodiment of a core body temperature wrist monitor.

The following detailed description provides a description of exemplary embodiments of the technology claimed here below to facilitate an understanding of the technology, but does not limit the scope of the technology claimed.

The term "exemplary" as applied to embodiments means "an example of." The term "heat trap" means a structure that is designed to receive incoming thermal energy, trap that thermal energy and minimize losses of thermal energy from its structure. An exemplary embodiment described herein has a shell of a material that is resistant to thermal energy passing through it (i.e. it is a "thermally insulative" material, or a "low thermal conductivity" material) with an inner thermally reflective surface that may include a coating or lining of a heat reflective material.

As a preliminary matter, there are several factors that may, or ought, to be taken into account in making a determination about whether an individual is exhibiting a febrile condition. A key factor is the person's core body temperature (TC).

However, TC varies from one individual to another, and is therefore not precisely constant for all persons, although 98.6° F. is regarded as "normal," i.e. not febrile. A more accurate determination of whether a person has a febrile condition is to accumulate a database of that person's temperature over a period of time and to obtain a baseline or cluster of TC from that data for that individual. Excursions from that base TC could then be assessed statistically as to any upward or downward trend with a degree of confidence regarding whether that particular person has a TC outside of his/her own normal range. However reading TC is often invasive, and requires both the time of the individual and a professional, as well as close human contact and object contact. When using a professional person to detect temperature and using a contact measurement protocol for population screening on a large scale where (it is anticipated) that 99.9% of the subjects are not febrile, creates cross contamination issues risking the spread of infection. This risk of spreading the infection may be greater than what the screening process was designed to prevent, under these circumstances. The costs, inconvenience, and cross contamination problems create both a real and/or perceived diminishing return for such a large scale effort. Accordingly, skin temperatures TS are measured and these are far less reliable as indicia of a febrile condition because human bodies release heat and also adjust the heat released based on ambient temperature conditions.

The following examples of the inventive technologies address these temperature-related issues and bring solutions to some commonly encountered situations. For example, it is desirable in many facilities, such as hospitals and nursing homes, to minimize risks of spreading any kind of infectious illness. One way of addressing that issue is to identify febrile persons and to take steps to either exclude those persons from the facility or take suitable precautions. Thus, examples of a "gate-keeper" technology of identification, temperature detection, and febrile condition determination are presented. Also presented are examples of devices that a user wears and that determine his/her condition as febrile or not.

Referring now to FIGS. 1, 2 and 3, the core body temperature wrist monitor 100 has a casing 110 with an upper surface 102 and an under surface 106. The under surface 106 is intended to be pressed gently against the inner portion of the wrist of an individual using the monitor 100 such that it rests comfortably at a position on the wrist proximate, where a pulse would normally be taken. The upper surface 102 is intended to face outward such that the wearer can read any indicia on the optional display panel 104. Further, the monitor 100 has a wrist band 105 that may be integrally formed with the casing 110, or that may be attached to the casing 110, as shown in the example of FIG. 1. Further, the under surface 106 may have a separate shield or cover 123 that covers an opening 122 of a heat trap 120 (not shown in FIG. 2), as explained here below. It may also have a soft and yielding O-ring-shaped comfort ring 112 that at least partially surrounds the opening 122 (of the heat trap 120, not shown in FIG. 2). The comfort ring 112 may provide a degree of wearer comfort and more importantly provide a seal between the opening 122 and the skin of the wearer. This should reduce or minimize potential heat losses between the wearer's skin and monitor 100 to the environment. Desirably, the material of the comfort and heat loss minimizing ring is non-allergenic, has, low thermal conductivity, and is soft and yielding. Desirably, but not necessarily, it may be at least partially embedded in a groove in under face 106. Other heat loss minimizing structures, such as partial rings, may also be useful.

Referring particularly to FIG. 3, when an exemplary core body temperature wrist monitor 100 is worn on the wrist 150, as shown, thermal energy (arrows 155) emanates from the wrist 150 to the environment. This thermal flow ("heat flow") arises because the user's core body temperature (TC) is higher than the ambient surrounding air temperature (TA) and will theoretically continue to until TC=TA; i.e. heat will flow until there is no temperature gradient to drive heat flow from the body to the surroundings. When heat flows into heat trap 120 through opening 122 of the heat trap 120, that heat is trapped within the heat trap 120. This arises because heat trap 120 has a surrounding shell 125 of a material that is a good heat insulator. Moreover, the shell 125 has an inner heat reflective surface 126. Over a relatively brief period of time after a wearer is fitted with the wrist core body temperature monitor 100, the heat energy that accumulates in the heat trap 120 causes the temperature TT in the heat trap 120 to gradually increase and to approach the core body temperature TC. Theoretically, once TT is equal to TC, no further heat can flow into the heat trap 120 because there is no longer a heat gradient (TC−TT) between the core body temperature TC and the temperature TT in the heat trap 120 to act as a thermal driving force. In practice, of course, there are always minor heat losses from the heat trap 120 so that heat flow will continue from the body to the heat trap 120. But, with an efficient heat trap 120, the heat flow out of the trap will be minimized so that the temperature within the heat trap will closely approximate or equal the core body temperature within the limits of accuracy required and/or provided by suitable temperature sensors.

An exemplary heat trap 120 is illustrated in FIG. 3, a partial cross sectional view of an example of a core body temperature monitor 100. This particular heat trap 120 has a domed shell 125, but other shapes may be used, as convenient. The shell is fabricated or formed of a material resistant to heat transfer through it. For example, the shell 125 may be formed of polystyrene, silica aerogel, fiberglass, and like materials. It is desirable, but not necessary that the material have a low thermal conductivity. In addition, it is desirable, but not necessary, that the material be lightweight (i.e. have a low bulk density) so that the wrist monitor is neither bulky nor heavy on account of the mass or bulk of the heat trap.

Figure 4:
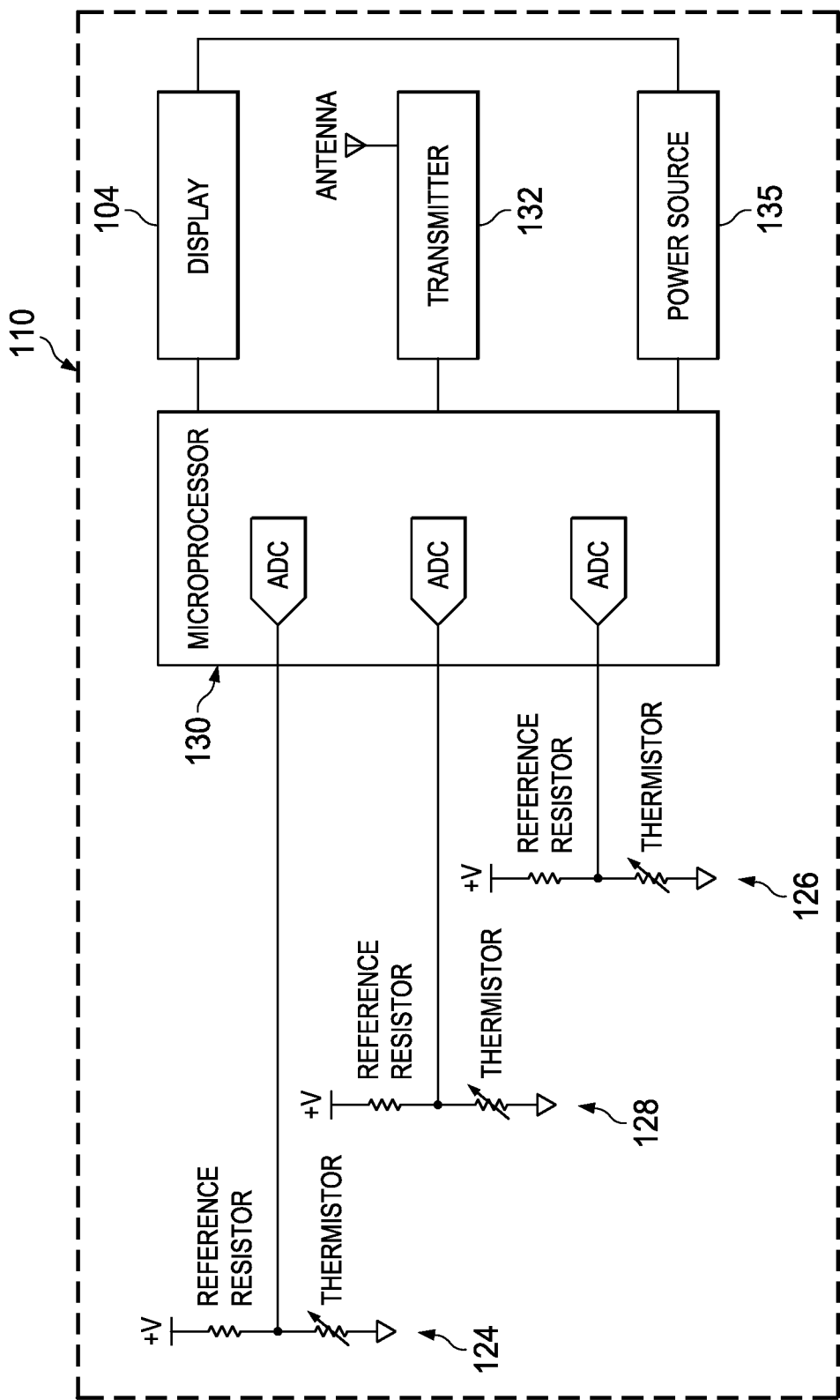
FIG. 4 is a block diagram showing electronic detail for an exemplary core body temperature wrist monitor.

The heat trap 120 is supplied with a reflective inner surface 126. This surface 126 may be created by the adhering of a material such as a metalized biaxially-oriented polyethylene terephthalate (BoPET) film, for example, metallized MYLAR® film [MYLAR is a registered trademark of DuPont Tejjin Films of Chester, Va.]. Other examples of an inner reflective surface include, but are not limited to, metallic foils and the like. In addition, as an alternative, the inner surface 126 may simply be of a sprayed on reflective metallic paint, such as aluminum, gold, copper, silver, and the like To measure the temperature TT in the heat trap 120, the exemplary embodiments of FIGS. 1-3 use a first temperature sensor 128 that extends into or along an inner surface 126 of the heat trap 120. The sensor 128 is electrically coupled to a microprocessor 130, as shown in FIG. 4. The temperature sensor 128 may be a thermistor, a thermocouple, or any other convenient sensor that can provide input to a microprocessor 130, with or without signal conversion from analog to digital Microprocessor 130 communicates the sensed temperature TT to the transmitter 132, also shown in FIG. 4. Power for the monitor 100 is supplied by a power source 135 within the casing 110. The power source may be a simple replaceable battery of the type used in watches or hearing aids, or may be a rechargeable battery, as desired. One of the considerations in selecting a battery type depends upon the nature of transmitter 132. If transmitter 132 is selected to have a long range or to broadcast in a high energy using protocol, that may dictate a high energy density battery, such as lithium ion or another high energy density battery for increasing the time of use between necessary battery recharge or replacement.

The wrist monitor 100 also has a second temperature sensor 124 that is located at a periphery of the casing 102 of the monitor 100, as best seen in FIG. 2. This sensor 124 clearly does not measure the core body temperature TC because it is in an area where heat flows continuously to the environment from the wrist 150 of the wearer and is not trapped. Thus, the temperature at the periphery will not reach core body temperature TC, but will provide a body skin temperature TS. The skin temperature TS may be expected to vary with ambient temperature TA, and also to vary with other factors (for example, clothing/glove and degree of physical exertion). As shown in FIG. 4, this temperature TS is also transmitted to microprocessor 130 and thence to the transmitter 132.

The wrist monitor 100 has a third temperature sensor 126 that measures ambient temperature (TA). This temperature may be used along with TS to estimate TC using an equation, below.

Optionally, as shown in FIGS. 1-2, the wrist temperature monitor 100 may have a display panel 104. The microprocessor 130 is in communication with this display panel 104 to provide input for display. The wrist monitor 100 may display both core body temperature TC as well as skin temperature TS, sequentially or simultaneously, or only the core body temperature TC. Further, it can also display, a calculated difference between the two, if it is of interest.

In order to determine with a higher level of confidence whether a wearer has a fever, it is desirable to have a series of core body temperature readings of that individual over a period of-time at useful intervals. The period of time may be all the time that the wearer is in an environment where he or she must be monitored, or any other time. The period between readings may vary from continuous readings to readings only every 5 minutes, or 30 minutes, depending upon the situation. However, these readings should be accumulated in a file or database and the readings should be subjected to analysis to estimate with a high degree of confidence whether the wearer has a fever.

In another embodiment, the wrist monitor 100 is supplied with a memory able to store data, including time and temperature readings, in a database. Further, the wrist monitor may be supplied with a processor able to execute a calculation to determine core body temperature. When a TC excursion from the normal is of sufficient magnitude that is predetermined to justify a determination of a significant risk of febrile condition, the wrist monitor may indicate an alarm condition audibly, or visually, or both. In addition, it may transmit a signal to alert appropriate parties.

Figure 5:
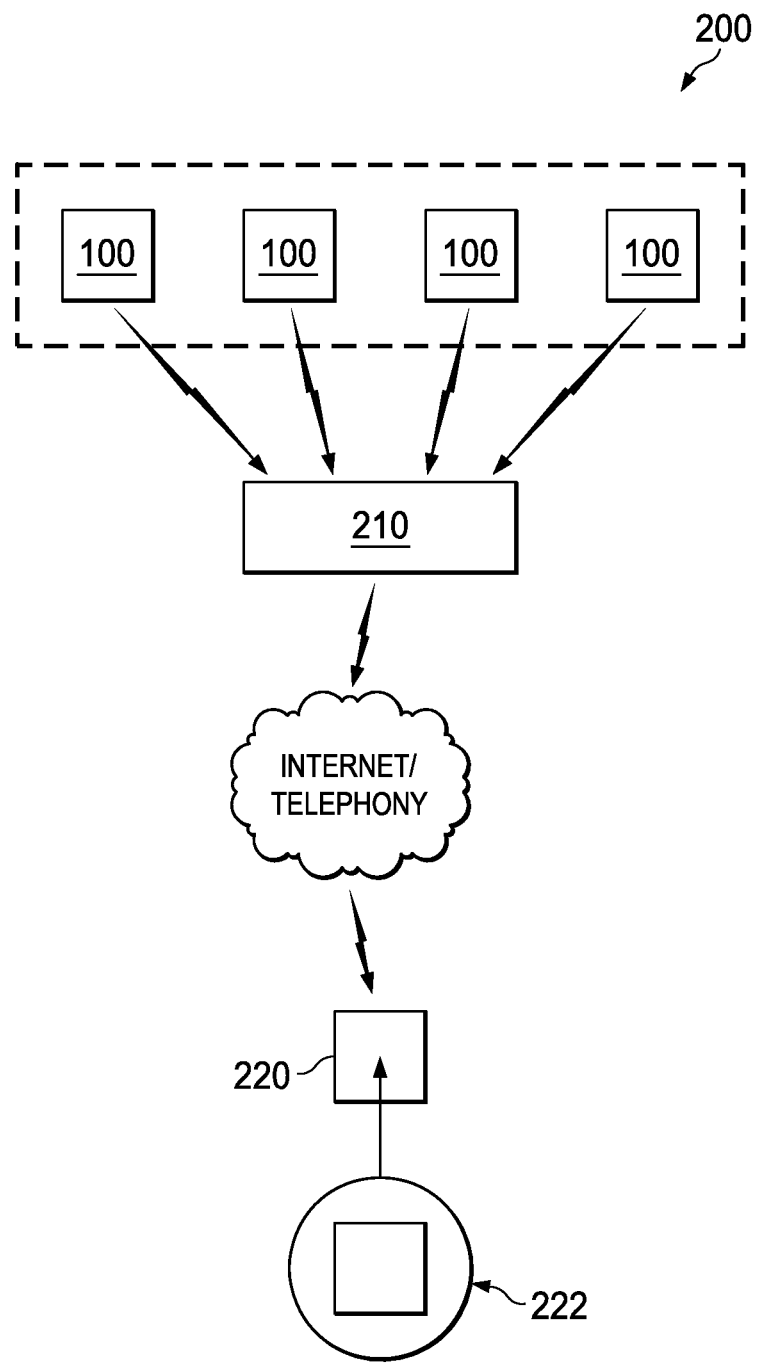
FIG. 5 is a diagram showing an exemplary system using core body temperature wrist monitors to monitor core body temperatures of a plurality of individuals.
Figure 6:
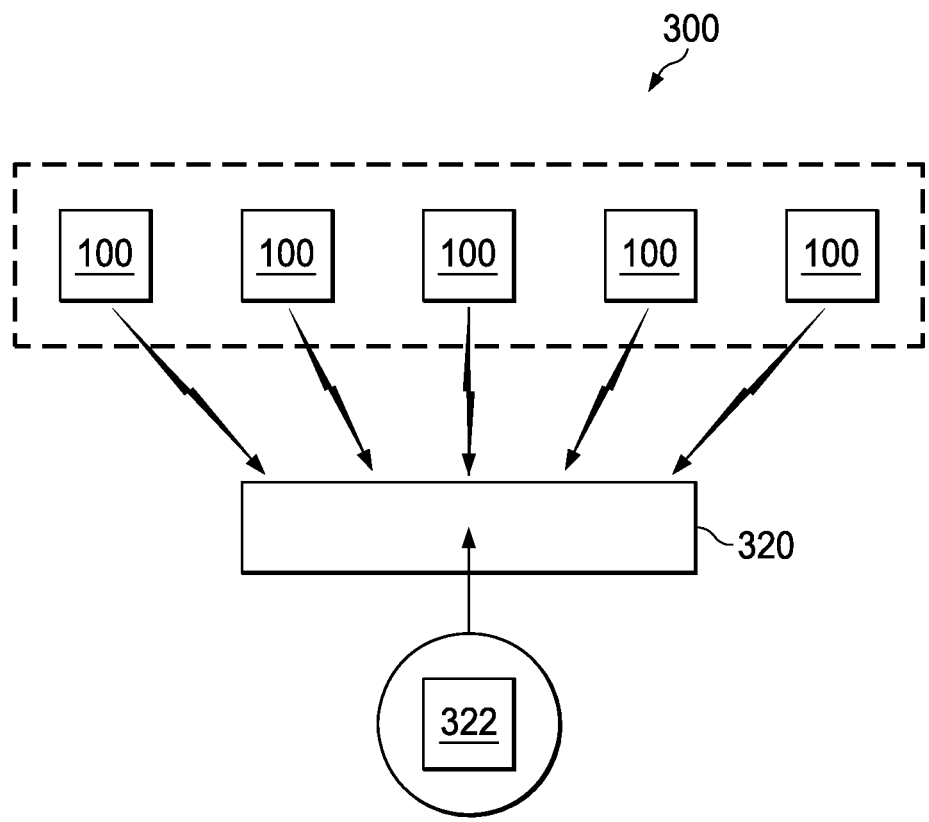
FIG. 6 is a diagram showing another exemplary system using core body temperature wrist monitors to monitor core body temperatures of a plurality of individuals.

Two exemplary systems for monitoring core body temperature wrist monitor wearers are shown in FIGS. 5 and 6. However, other systems are also useful to accumulate wearer temperature data and to determine whether or not the wearer has a fever.

In the example of FIG. 5, the system 200 includes wrist monitors 100 transmitting information to a receiver-transmitter 210. The transmitting of information may be by any suitable wireless protocol. Desirably, to conserve wrist monitor power, the transmission is of a kind that minimizes power usage. Non-limiting examples include Bluetooth, WiMax, digital telephony, and the like wireless protocols. The information transmitted includes the time, the sensed temperatures (TC, TS and TA). Of course, other data may also be transmitted, if required or desirable. The receiver-transmitter 210 in turn transmits the information to a server (computer) 220, for example, via WiFi over the Internet, Bluetooth, telephony (e.g. 3G or 4g systems) or any other wireless protocol suitable under the circumstances.

The server 220 includes a database 222 in its memory. An exemplary database includes a separate segment for each wearer that also has fields for input of new information as received from the receiver-transmitter 210, and storing this information for processing. The information from the database is processed to determine whether a wearer, identified by his database file, has a fever. Thus, at periodic intervals that may be programmed into the server 220, the following calculation is made:

$$TC=(1+h/pc)(TS-TA)+TA$$

where h/pc is estimated at about 0.19

The term h/pc is a coefficient used to approximate the heat loss at skin temperature based on three parameters: h, which is empirically derived; p the perfusion rate; and c the specific heat of blood. These parameters vary based on the tissue being measured and is clearly lower for tissue that is closer to core temperature such as oral, ear drum/canal and then higher for extremities. In general, the ratio h/pc may vary from about 0.05 to about 0.50.

The foregoing calculation provides an estimate or prediction of a fever condition with a high level of confidence and low number of "false positives." This is a significant advantage since a high number of false positives may result in losses in certain environments, for example in a work place where a worker will be sent home. A better indication of h/pc may be arrived at by comparing empirical data (comparing, for example, TC measured by a reliable standard versus TC calculated using the wrist monitor) for a particular wrist monitor design. False positives are regarded as statistical "outliers" in any recording of clusters of temperatures in one minute or other short time intervals. Outliers can be one standard deviation or more away from the most recent ten minute cluster thereby creating the most valid positive febrile detection window of approximately 20 minutes.

In an alternative example of a system 300, the receiver-transmitter 210 is not necessary. Instead, the wrist monitors 100 transmit information directly to the server 320 that has a database 322. The transmission protocols may be selected for suitability of purpose and the power supply and power usage for the monitors 100. The database 320 may be like database 220 described above, and the calculations to estimate fever may be the same or similar.

The database is organized by the unique identity of the sensor paired to a unique identity of the person. This arrangement in the database permits reuse of the sensor by other individuals as well as the ability to view any measurement biases that a given sensor may be exhibiting across different individuals. Thus, if necessary action may be taken to compensate for any known tendencies of a particular sensor. The schema for the database is extensive, covering historical records for all individuals on a historic basis in a single day's record as well as a table of current measurements for every individual. The database records also include the current reader identity so as to give information on the physical proximate location of the sensor in the network.

In a further aspect, the technology is also directed toward controlling the access of persons having a detected febrile condition to a particular facility, which may be a hospital, nursing home, school, place of work, manufacturing facility, or indeed any place where such screening may be deemed useful or necessary. Exemplary embodiments of this aspect are illustrated in FIGS. 7 and 8.

Figure 7:
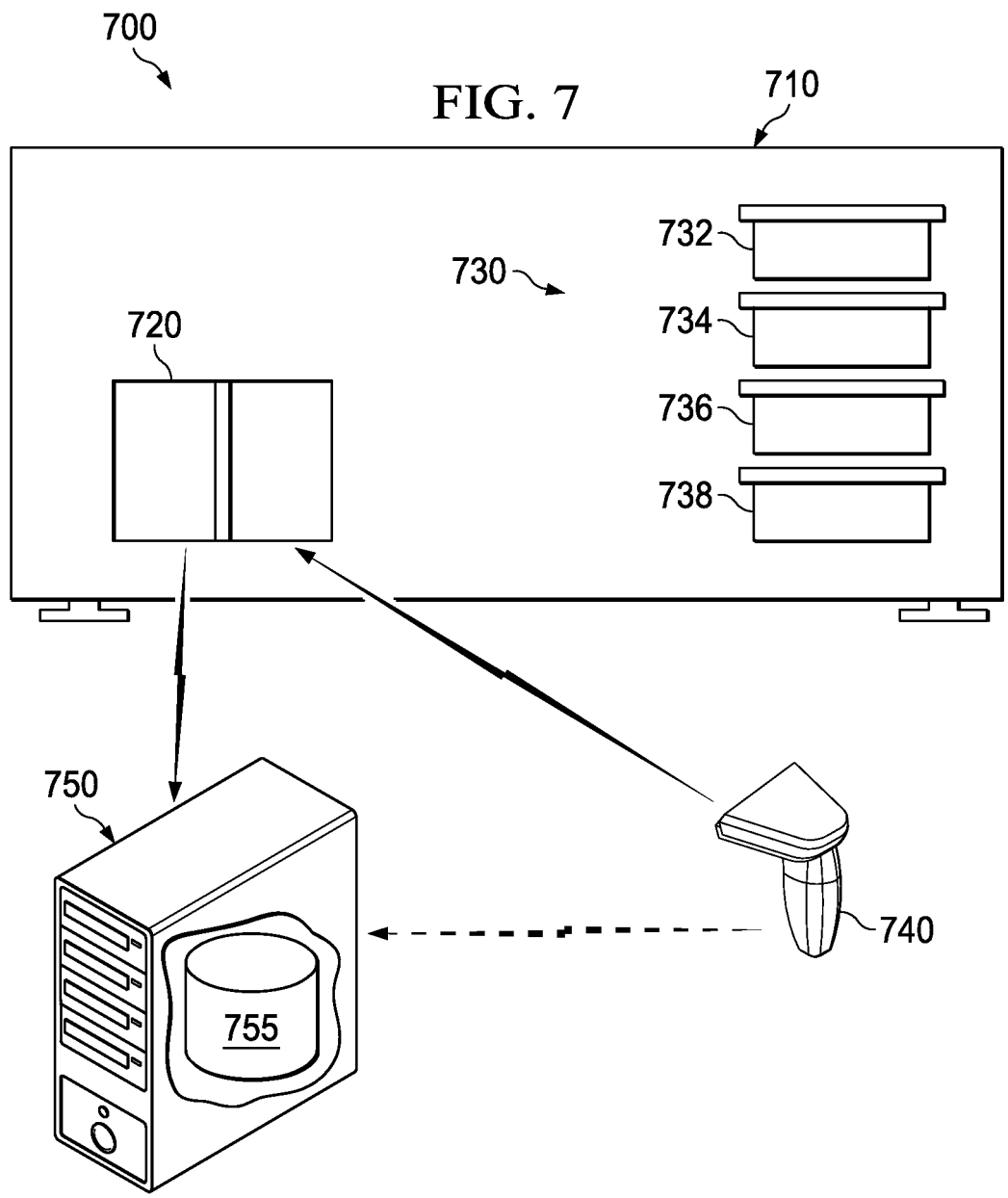
FIG. 7 illustrates an exemplary embodiment of a system for screening and identifying persons with a febrile condition seeking entry to a protected area in which febrile persons must either be identified, or from which they must be excluded.
Figure 8:
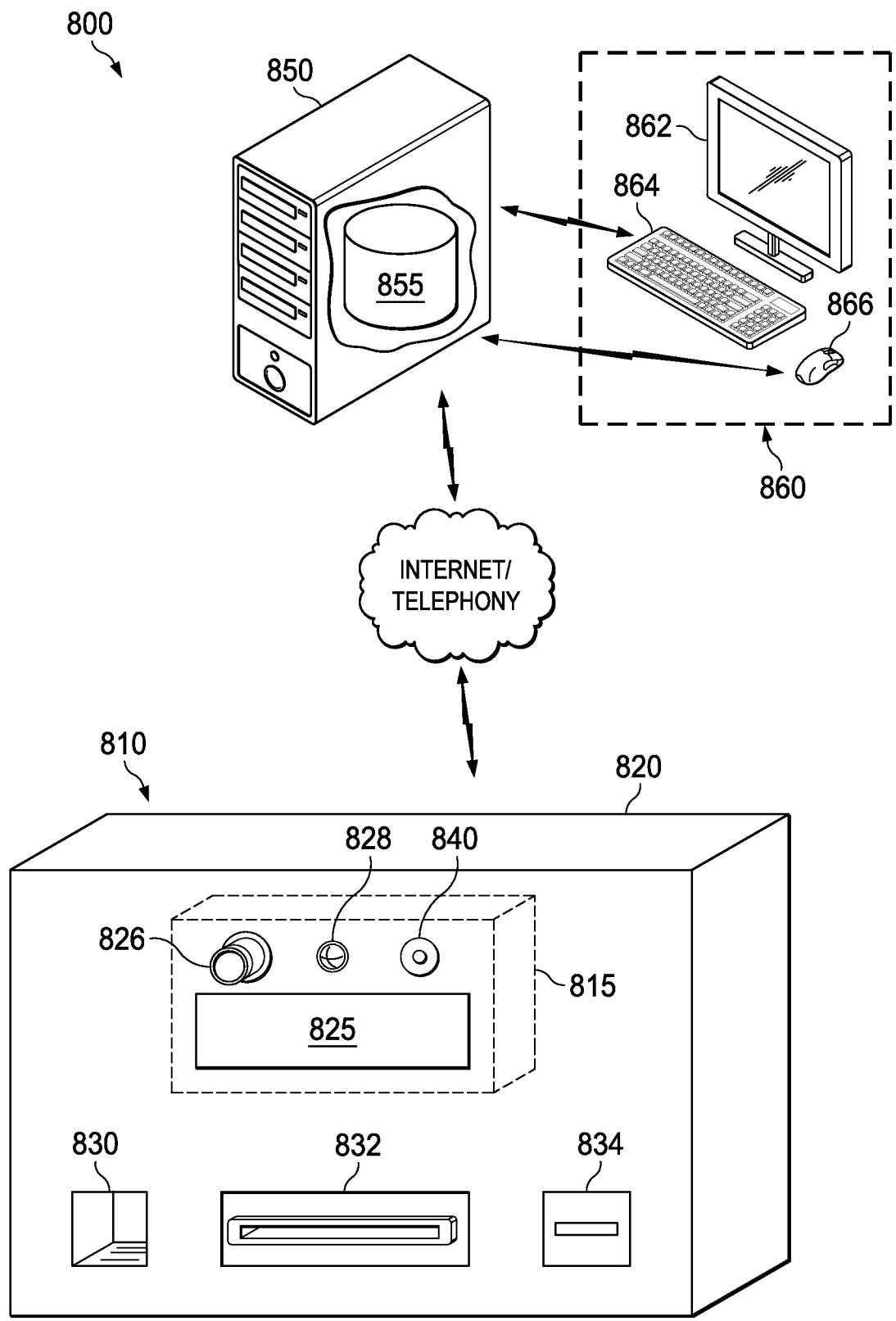
FIG. 8 illustrates another exemplary embodiment of a system for screening and identifying persons with a febrile condition seeking entry to a protected area in which febrile persons must either be identified, or from which they must be excluded.

FIG. 7 illustrates an exemplary system 700 for screening and identifying persons with a febrile condition, preferably located at a "gateway" to a protected area in which febrile persons must either be identified, or from which they must be excluded, until further action may be taken, or to which they may be allowed access subject to restrictions. System 700 may include a station 710 to which is mounted a detector-transmitter 720 and a dispenser area 730. The dispenser area 730 may be compartmentalized or may include separate dispensers, such as a dispenser for gloves 732, a dispenser of tissue paper 734, a dispenser for masks 736, and a dispenser of a liquid or cream of an anti-bacterial formulation 738. The detector-transmitter 720 may include any of: a bar code scanner, a RF detector for a smart card, and/or a biometric type of identifying device such as, for example, a hand/fingerprint scanner, a card reader, or an optical scanner that may be used to uniquely identify an individual and present indicia readable by the detector-transmitter 720. Further, the system 700 includes a temperature reader 740 with built in temperature data transmission capability. The temperature reader 740 may utilize an infrared sensor, the "heat trap" technology detailed above, or any other temperature detection technology that is accurate, precise, rapid and non-invasive. Temperature reader 740 may be releasably mounted to the station 710 by a holder 742. Temperature data from the temperature reader may be transmitted to the detector-transmitter 720 via an RF transmitter, a Bluetooth transmitter or any other suitable transmitter. The detector-transmitter 720, which may be battery or electrically powered, transmits received data to a server 750, via the Internet by WIFI, by wired connection, by RF transmission, by Bluetooth transmission, WiMax, wireless telephony, or any other suitable mode of data transmission. Alternatively, the temperature reader 740 may transmit data directly to the server, if that is more convenient and the transmitter of the temperature reader 740 has the capability. The server 750 has a database 755 for compiling data about each of a plurality of individuals that are allowed access to the protected area, including pertinent data about their identities, respective scanning times for entry times at the facility, their temperatures, and other pertinent data, as necessary and useful for a particular facility.

The exemplary system 700 operates as follows: a person requiring ingress to the area that is being protected presents a form of identification readable by the detector-transmitter 720. This data is checked against the database 755 of server 750. If the person is authorized, with identifying data present in the database, he is then required to be scanned or self-scan for temperature using the temperature reader 740. The detected temperature, date and time is transmitted to the detector transmitter 720, or directly to the server 750, and recorded in the data file of that person in database 755. If a febrile condition is detected, an alarm (audible or visual, or both) is generated to notify responsible parties and a note may be placed in the person's data file in database 750. Detection of a febrile condition may be facilitated using the equation provided above, with appropriate correction for h/pc, as explained above. A person with temperature recording will be better detected for febrile condition or "outlier" from his/her normal temperature cluster. Such a person with a detected febrile condition or outlier may have his access restricted, allowed, or denied. Often the person may be guided by human resources guidelines that may dictate specified actions depending upon the job responsibility of the person. Greater protections, such as masks and gloves, may be required for personnel experiencing low grade fevers in ICU or kitchens as opposed to those persons working in other less critical areas.

As an added functionality, the system may optionally include a dispenser 730 from which the person seeking to enter the protected area may take gloves, masks, and tissues, and where he might clean his hands with an anti-bacterial formulation, before entering.

In a further exemplary embodiment, a system 800, illustrated schematically in FIG. 8, includes a self-contained user-interface unit 810 that may be located at the entry point to a space from which it is desired to exclude persons with a febrile condition, or at least identify them for alternative action. Such spaces may include, but are not limited to, hospitals, nursing homes, schools, places of business, manufacturing facilities, etc. Further, user interface unit 810 may be enclosed within a housing 820 as shown in the example, or may be built into a convenient area in the vicinity of the entry point of the facility or department within the facility, such as a wall near an access doorway, as long as the components of the user-interface unit 810, described below, are accessible for maintenance and repair, as needed, and the function of the user-interface unit 810 is not impaired. The user interface unit 810 includes within housing 820 a "computer" 815 (shown in dashed lines), such as for example, a tablet PC or the equivalent, such as an iPad® (trademark of Apple, Inc. of Cupertino, Calif.) that has wireless capability, and a screen. In exemplary embodiments, the convenience of a tablet computer provides some advantages but, other devices may also be used. In other exemplary embodiments, the computer 815 may be selected from tablet devices using the Android™ operating system (product and trademark of Google of Mountainview, Calif.), Windows® (a registered trademark of Microsoft Corp. of Redmond, Wash. State), or any other suitable operating systems. Preferably, but not necessarily, computer 815 may also have a front facing camera. Thus, the screen 825 of computer 815 is viewable and touchable (if a touch screen is used) through a window in housing 820. The screen may display several menus to guide a user through the identification, temperature detection and screening process.

The exemplary embodiment includes several alternative and optional features for recognizing a person seeking automated permission for access or to work in a facility protected by the system. These may include a camera, whether part of the computer 815 inside housing 820 or a separate camera, has a lens 826 that is able to capture data for facial recognition applications software technology. This facial recognition technology may be installed on the computer 815 to compare with facial data stored on a database on a memory on the computer 815 or at a remote database 855 on a server 850. Or, the applications software may be installed on a remote server 850 that has a database 855 with stored facial recognition data. The remote server 850 may be accessed in any of a number of ways: wirelessly via the internet, by hard wire connection, by local area network, and the like, as appropriate and convenient. Further, and optionally, in the event of dim light, a light source 828 is provided as well to assist facial recognition technology. A narrow beamed light may also be used to provide feedback on the video image from the camera regarding where the narrow beamed infrared sensor is currently aimed.

An individual seeking entry may also use a fingerprint ID pad 830 that collects data, and transmits it to a computer to identify the individual by comparing with stored data in a database. The applications software and fingerprint identification data for individuals may be stored either in the computer 815 in the housing 820 or at remote server 850, as described above in the case of facial recognition. The software user interface is designed to obviate the keyboard and minimize or eliminate touch, if possible. The addition of a fingerprint reader and software/camera based facial recognition minimizes this user touch. Presently, fingerprints are still far more consistently secure than facial recognition, by more than an order of magnitude. However, that situation is expected to change in the future as these technologies develop. Thus, only if the preset software confidence level of the facial recognition is insufficient for a presenting user, is the user asked for his/her fingerprint. This permits access with a single touch to the tiny fingerprint reader. The fingerprint access in turn positively reinforces the presenting face, which it did not provide a sufficiently high confidence level initially by itself to permit access.

In a further alternative, an individual issued with a tagged access card may identify by using a card reader 832. These card readers may be of any kind that is deemed suitable for the facility. For example an RF card reader, a bar code reader, a magnetic strip reader, and other reader suited to the type of card used by the facility. In addition, if upon identification of the individual, it is desired to predetermine the length of stay of that individual in the facility, the user interface unit 810 may include a time-sensitive tag dispenser so that this indicator may be displayed on the user's card to indicate the user's status as either "current" or "expired."

An identified person may be scanned with an infra-red (IR) temperature scanner 840 to determine a skin temperature (TS) by scanning a convenient area of the person, such as the forehead, or an inner area of the wrist Since the scanner 840 is in the facility, it also has a read of the ambient temperature (TA). Using these two readings that are both transmitted to the computer 815, the core temperature (TC) of the individual may be estimated using the following relationship equation:

$$TC = (1 + h/pc)(TS - TA) + TA$$

where $h/pc = 0.19$

The actual calculation may be carried out either at computer 815 or at remote server 850. The result is compared with previous readings of TC for the particular individual. Based on the TC reading and the statistical distribution of readings for the particular individual in a non-febrile state, a determination can be made with a statistical confidence level as to whether the individual is febrile. The results may be displayed on screen 825, and may also be displayed at a remote location 860 equipped with a user interface, such as the illustrated exemplary monitor 862, keyboard 864 and mouse 866. Thus, an authorized individual may screen persons from entry (or take other action) based on both his or her identification credentials, as well as his or her temperature results as detected and calculated.

In an exemplary embodiment, the narrow beam scanner 840 may optionally include one or two PC controlled USB-based servo controls, such as the Futaba S3111 (manufactured by Futaba of Chiba, Japan) fixed to 840. One control may be used to scan vertically and one control may be used to scan horizontally, all the while making rapid measurements in each area of the scan. This scanner has several benefits enumerated below:

1. Scanning permits the software to seek or accept instruction as to the best locations in space where room (ambient) temperature can be read. This can be done anytime a person is not standing before it, or if so programmed, during a facial scan.
2. Full narrow focus infrared scanning of the face is to obtain a maximum heat measurement over the face or neck indicative of the area of the closest blood flow to the surface. Theoretically, and in practice, this area is often the temporal artery found on each of the two sides of the forehead.

3. By noting the temperature contours of the face in the database, algorithms may be refined to further reduce any false positives as well as anomalous dermatologic conditions that the user might request.
4. As the device may be mounted to a wall, the ability to scan means that a tall person will not be inconvenienced by stooping or a short person by standing on a stool. The scanner will be able to heuristically find the person's face because the facial temperature characteristic is unique. This might also provide (to application software) further information to establish identity with greater certainty, such as the person's approximate height in their shoes.

Exemplary commercially available infrared sensors for these purposes, with accuracy and repeatability sufficient to permit, with common in situ calibrations techniques, may have accuracies exceeding +/−0.25° C. These sensors come in mixed technology formats and in some cases even in completely integrated chip form. Non-limiting examples of mixed sensors that are useful include, but are not limited to, Raytek (of Santa Cruz, Calif.) RAYCMLTJ and chips such as the Texas Instruments (of Dallas, Tex.) TMP006. The TMP006 is suited for a simple integrated tablet or built-in handheld peripheral suited to this invention.

The foregoing description provides examples of embodiments of the wrist core-body temperature monitors, and embodiments of access point temperature-based screening systems, and does not limit the inventions, which are defined only by the appended Claims. The scope of the inventions includes any modifications and supplementations that a person of ordinary skill in the art may perceive upon reading this disclosure. Further, the scope of the claimed inventions includes any equivalents that a well-informed court may provide under the doctrine of equivalents.

The invention claimed is:

1. A system for identifying persons and screening the persons for a febrile condition, the system comprising:
   identifying a person using data input by the individual or detected from indicia of the person and previously stored data about the person;
   detecting a temperature condition of the person;
   determining whether the person has a febrile condition using the detected temperature condition and previously stored temperature data of the person; and
   taking action to restrict ingress, deny ingress or allow ingress based on the determined condition of the person requiring ingress.

2. The system of claim 1, further comprising providing an alarm when a person requiring ingress has a febrile condition.

3. The system of claim 1, wherein the step of transmitting temperature data includes transmitting the temperature data to a first transmitter so that the first transmitter transmits the read data to a server.

4. The system of claim 1, wherein the identifying is by facial recognition, finger print detection, or by reading a user card.

5. The system of claim 1, wherein the detecting of a temperature condition is by infra-red detection.

6. The system of claim 1, wherein the step of determining a temperature condition includes using a formula of the form: $TC=(1+h/pc)(TS-TA_r)+TA$, where $h/pc$ is from about 0.0 to about 0.5.

* * * * *